United States Patent [19]
Stefan

[11] Patent Number: 6,100,314
[45] Date of Patent: *Aug. 8, 2000

[54] ADHESIVE SYSTEM FOR DENTAL PURPOSES

[75] Inventor: Klaus-Peter Stefan, Seefeld, Germany

[73] Assignee: ESPE Dental AG, Seefeld, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 09/074,690

[22] Filed: May 8, 1998

[30] Foreign Application Priority Data

May 12, 1997 [DE] Germany .............................. 197 19 890

[51] Int. Cl.⁷ ...................................................... A61K 6/083
[52] U.S. Cl. ............................ 523/118; 523/116; 522/24; 522/28; 433/228.1
[58] Field of Search ..................................... 523/116, 118; 522/28, 24; 433/228.1

[56] References Cited

U.S. PATENT DOCUMENTS

| | | | |
|---|---|---|---|
| 5,133,957 | 7/1992 | Sum et al. ............................... | 523/118 |
| 5,320,886 | 6/1994 | Bowen ..................................... | 523/116 |
| 5,498,643 | 3/1996 | Antonucci et al. . | |
| 5,530,038 | 6/1996 | Yamamoto et al. ...................... | 523/118 |
| 5,645,429 | 7/1997 | Blackwell et al. ....................... | 523/115 |
| 5,814,682 | 9/1998 | Rusin et al. ............................. | 523/116 |

FOREIGN PATENT DOCUMENTS

| | | |
|---|---|---|
| 41-05550A1 | 8/1992 | Germany . |
| 93-12760 | 7/1993 | WIPO . |

OTHER PUBLICATIONS

R. Janda, Karben, Polymere Materialien fur adhasive prophylaktische und restaurative MaBnahmen–I. Teil, ZWR, 101. Jahrg. 1992, Nr.7, pp. 498, 501–506.

*Primary Examiner*—Andrew E. C. Merriam
*Attorney, Agent, or Firm*—Birch, Stewart, Kolasch & Birch, LLP

[57] ABSTRACT

The invention relates to an adhesive system for fixing dental restorative materials to hard dental substance constituting i) a component which contains at least one activator which is a constituent of a chemical initiator system, and contains at least one ethylenically unsaturated compound which is capable of polymerization, ii) a component which contains at least one ethylenically unsaturated compound which is capable of polymerization but otherwise contains no further activator, which is able to start chemical curing with the activator from component i), and iii) a dental restorative material which contains at least one activator which, together with the activator from i), is able to start a polymerization reaction, or a cement for fixing dental restorative materials that have already cured, which contains at least one activator which, together with the activator from component i), is able to start radical polymerization.

5 Claims, No Drawings

ADHESIVE SYSTEM FOR DENTAL PURPOSES

FIELD OF THE INVENTION

The present invention relates to an adhesive system for the durable fixing of dental restorative materials such as composite filling materials, inlays, onlays, crowns, bridges, ceramics, veneers, and Maryland bridges to a hard dental substance.

BACKGROUND OF THE INVENTION

Well known systems for bonding such restorative materials to teeth are usually composed of three components. Component 1 contains an acid (e.g. phosphoric acid or maleic acid) for partially etching the dental enamel and the dentine, component 2 contains hydrophilic crosslinkable compounds which flow well onto the hard dental substance, and component 3 contains crosslinkable substances which combine well with component 2 but are markedly more hydrophobic than dental enamel and dentine. Mostly, component 3 also contains one or more photoinitiators by means of which the adhesive system is hardened by irradiation with light. Such pretreatments for the adhesive bonding of hard dental substance to restorative materials are described, for example in U. Blunck, Quintessenz (1996), 47 (1), 19–35; R. Frankenberger, N. Krämer, J. Sindel, Dtsch. Zahnärtzl. Z. (1996), 51, 556–560; and A. Pagliarini, R. Rubini, M. Rea, C. Campese, R. Grandini, Quintessence International (1996), 27, 265–270. As can be derived from these literature citations, dental surfaces pretreated in this way combine well with the corresponding dental materials and lead to a durable bond between restorative material and tooth.

In previous years, adhesive systems were also developed which unite components 2 and 3 in one component in order to reduce the overall work required for the fixing procedure, as described, e.g., in EP-A-0 234 934 and 0 305 083.

A disadvantage of the light-curing adhesive systems described is that the thickness of the fixing film that occurs can not be controlled accurately and is no longer flexible due to curing by means of irradiation. When inlays or onlays are used, this leads, for example, to an undesirable increase in the preparation and thus adversely affects the accuracy of fit to a considerable extent. As can be derived from the ISO standard 9917, even film thicknesses of the adhesive system of more than 25 $\mu$m lead to accuracies of fit that are no longer acceptable, which means a considerable amount of extra grinding work for the dentist and, in unfavourable cases (e.g. due to breakage of an inlay during bite control), make it necessary for the dental technician's work to be done afresh.

In order to overcome these disadvantages, adhesive systems were developed which, instead of the components 2 or 3 described above, contain two partial components 2a and 2b and 3a and 3b respectively, which are mixed together before being applied to the hard dental substance (see, e.g., "Clearfil Line Bond 2" in Reality now, 1996, 80, 2). As a result of this mixing, a chemical curing process is started, which causes the entire adhesive system to cure within a few minutes. As a rule, however, the person carrying out the treatment still has sufficient time before curing is complete to apply the restorative material to the preparation in which the adhesive system is still sufficiently flexible to achieve a sufficient accuracy of fit. Any excess adhesive system can be pressed out at the edge of the preparation.

A disadvantage of these adhesive systems is their relatively labour-intensive application process since, compared with the radiation-curing systems described at the beginning, one more component and one more mixing stage is required (component 2 or 3 is composed of two compositions 2a and 2b and 3a and 3b respectively to be stored spatially separate from one another). This may easily lead to confusion on the part of the dentist and hence cause lasting damage to the adhesive power of the system. A further disadvantage of this adhesive system is the fact that the person carrying out the treatment is dependent on the setting time of the fixing system in question which can lead to unnecessary waiting times during the treatment or, in the case of more rapidly setting systems, may entail premature curing of the adhesive, with the same disadvantages as with light-curing systems.

SUMMARY OF THE INVENTION

The object of the present invention is, therefore, to provide a simple to use adhesive system which is flexible whilst a restorative material is being incorporated and then hardens rapidly, which system has good adhesion and guarantees a durable bond between dental restorative materials and the hard dental substance.

This object is achieved by providing an adhesive system which is composed of the following constituents:

i) a component which contains at least one activator, which is a constituent of a chemical initiator system, and at least one ethylenically unsaturated compound, which is capable of polymerisation, and a solvent for the activator and the unsaturated compound, ii) a component which contains at least one ethylenically unsaturated compound which is capable of polymerisation but otherwise contains no further activator, which can start chemical curing with the activator from component i), and iii) a dental restorative material which contains at least one activator which, together with the activator from i), can start a polymerisation reaction, or a cement for fixing dental restorative materials that have already cured, which contains at least one activator which, together with the activator from component i), can start radical polymerisation.

In a preferred embodiment, the adhesive system according to the invention additionally contains iv) an acid component which partially etches the dental enamel and dentine and acts as a pretreatment.

When this adhesive system is used, the person carrying out the treatment proceeds in such a way that he first applies component iv) to the hard dental substance, allows it to react for a certain time, and then rinses it off with water as is customary with other bonding systems as a pretreatment. Component i) is then applied in the form of a thin film to the hard dental substance. A thin film of component ii) is applied on top, and as a final stage the dental restorative material iii) is pressed onto the films of i) and ii) or the cement iii) is applied, and the dental restorative material that has already cured is pressed on to this. As a result of this pressing of component iii), a mixing of components i), ii) and iii) takes place, as a result of which the two activator components of the initiator system come into contact with one another and start the curing process. Surprisingly, even simple pressing of component iiii) is sufficient to bring about such a thorough mixing that the curing process is started in its entirety and comparatively good adhesion values are obtained as with conventional adhesive systems, as is proved in the Examples.

The advantage for the user lies in the fact that he needs to apply the individual constituents of the adhesive system i), ii) and iii) according to the invention only individually in succession and he himself can ultimately control the onset of the curing reaction by applying the restorative material. An interim irradiation with the disadvantages described above, or a time-consuming and unwieldy mixing of two components is not required with this method of operating.

DETAILED DESCRIPTION OF THE INVENTION

The invention is described in more detail below and explained further by examples.

Component i) is preferably a mixture of a suitable solvent which is capable of dissolving short-chain polar, ethylenically unsaturated compounds which are capable of polymerisation, and an activator which is a constituent of a chemical initiator system. Chemical initiator systems in this context are taken to mean those that are able to form radicals by mixing at least two chemically different substances without a further input of energy, which radicals are then able to initiate a polymerisation reaction. Examples of such chemical initiator systems are peroxy amine or peroxy proton donor/metal compound mixtures, of the kind described by J. M. Antonucci et al. in J. Dental Research (1979), 58 (9), page 1887–1889 or in U.S. Pat. No. 5,166, 117 and in EP-A-0 115 410, 0 115 948, 0 120 559 and 0 277 413. Component i) then contains, for example, either an amine or a peroxy compound or a corresponding proton donor. Moreover, component i) contains at least one ethylenically unsaturated compound which is capable of undergoing radical polymerisation.

Component i) need not contain a solvent if the constituents of component i) used are in themselves sufficiently free-flowing and hydrophilic. The use of a solvent is, however, preferred. Possible solvents for component i) are short-chain alcohols, short-chain ketones, aliphatic or unsaturated ethers, cyclic ethers and carboxylic acids and dicarboxylic acids. Particularly preferred solvents are water, ethanol and acetone.

Possible amines are alkylarylamines, dialkylarylamines, trialkylamines or derivatives thereof. Particularly preferred amines are N,N-bis-β-oxyethyl-3,5-di-t-butylaniline, N,N-bis-β-oxyethyl-4-toluidine, N,N-bis-β-hydroxyethyl-3,4,5-trimethylaniline and the amines described in DE-A-2 658 538.

Examples of peroxy compounds that may be used are diacyl peroxides, peresters, perketals, peroxydicarbonates, dialkyl peroxides, ketone peroxides or alkylhydroxy peroxides. Particularly preferred peroxy compounds are di-t-butylperoxide, t-butylperoxy benzoate, di-p-methylbenzoyl peroxide, dibenzoyl peroxide and dilauroyl peroxide.

Suitable proton donors are acids, amino acids, phenols, or hydroxy alkenes. Particularly preferred proton donors are sulphinic acids, barbituric acid, thiobarbituric acid and ascorbic acid.

Metals that may be used as an additive to increase the reactivity of the proton donor are copper, silver, cerium, iron, cobalt, nickel, vanadium and manganese. Corresponding metal salts or organometal compounds of the kind described, e.g., in EP-A 0 732 098, are also suitable.

Suitable ethylenically unsaturated compounds are those containing at least one double bond that can undergo radical polymerisation. These may be mono- or polyfunctional acrylates and methacrylates, of the kind described, for example, in EP-A-0 480 472. Moreover, functionalised monomers with terminal acrylate or methacrylate groups may likewise be used, of the kind described, e.g., in DE-A-2 312 559 and in EP-A-0 219 058. Of course, mixtures of said monomers may also be used.

The activator content, optionally dissolved in the solvent of component i), is between 1 and 40 wt. %, preferably between 5 and 20 wt. %, based on the total weight of component i).

The content of polymerisable compounds, optionally dissolved in the solvent of component i), is between 5 and 80 wt. %, preferably between 10 and 60 wt. %, based on the total weight of component i).

In addition, component i) may also contain conventional stabilisers and auxiliaries.

Component ii) of the adhesive system according to the invention contains at least one ethylenically unsaturated compound which is capable of undergoing radical polymerisation. These may be mono- or polyfunctional acrylates and methacrylates, of the kind described, for example, in EP-A-0 480 472. Moreover, functionalised monomers with terminal acrylate or methacrylate groups may likewise be used, of the kind described, e.g., in DE-A-2 312 559 and in EP-A-0 219 058. Of course, mixtures of said monomers may also be used. In addition, component ii) may also contain conventional stabilisers and auxiliaries. It is important that component ii) does not contain any activators at all that may form radicals together with the activator from component i). Conventional photoinitiators of the kind used in dental compositions may, however, be contained in component i).

Component iii) is a dental restorative material which contains at least one activator which, together with the activator from component i), is able to start radical polymerisation, or a cement for fixing dental restorative materials that have already cured, which contains at least one activator which, together with the activator from component i), is able to start radical polymerisation.

Possible activators of component iii) are those of the kind described for component i) or mixtures of said activators. In the event that a complete initiator system is present in component iii), component iii) must consist of two spatially separated parts which are mixed together immediately before the application of component iii) to component ii). The one part of component iii) then contains, for example, a peroxy compound, the other part an amine.

Dental restorative materials which may already contain activators are conventional composite filling materials. These may be either light-curing and are mostly in the form of a single paste, or they possess a self-curing mechanism in which case they are composed of two pastes spatially separated from one another.

Other dental restorative materials which are fully cured long before their adhesive fixing to the hard dental substance, such as, e.g., inlays, crowns, bridges, veneers or Maryland bridges, must be bonded to the adhesive system by means of a cement. Said cements may also be composite compositions of the kind described, e.g., in a review by McComb, "Adhesive luting cements—classes, criteria and usage", Compendium (1996), 17, 759–773, but must be sufficiently free-flowing or rendered sufficiently free-flowing by suitable methods such as, e.g. ultrasonics (described in EP-A-0 480 472) to be able to fill gaps in an optimum manner between restorative material and hard dental substance.

Both during the application of the restorative material, which already contains at least one activator which may react with the activator from component i), and during the application of dental restorations by means of a cement, a pressure is exerted on the films of the adhesive system according to the invention. This pressure leads at least to a partial mixing of the components i), ii) and iii), as a result of which the activators of components i) and iii) come into contact with one another and start radical polymerisation of the entire adhesive system. Component ii) which contains no activator is also polymerised in so doing.

Component iv) of the system according to the invention which is preferably present contains an acid constituent of the kind conventionally used in dental pretreatments. For example, acids which are suitable for this purpose are described by M. Buonocore in "The Challenge of Bonding to Dentin", The Acid Etch Technique, (St. Paul 1974). Component iv) may be used as a liquid or in the form of a gel. Commercially obtainable products that may be used as component iv) are, for example, Minitip® etching gel (Espe, Seefeld) or Esitcid®-G-Gel (Kulzer, Hanau). Component iv) is usually and preferably aqueous phosphoric acid.

The procedure described above leads to a good adhesive bond between hard dental substance and restorative material, as is proved in the examples that follow which are intended to describe the invention in more detail.

EXAMPLES

Reference Example 1

Example of preparation for component i) without activator:
40 g of deionised water, 50 g of hydroxyethylmethacrylate (HEMA) and 10 g of mono-(2-methacroyloxy-ethyl)-Mg-phosphate (Mg-HEMA-phosphate) are mixed together until a clear solution i-0) is obtained.

Example 1

Example of preparation for component i):
39 g of deionised water, 48.75 g of hydroxyethylmethacrylate (HEMA), 9.75 g of mono-(2-methacroyloxy-ethyl)-Mg-phosphate (Mg-HEMA-phosphate) and 2.5 g of N,N-bis-β-hydroxyethyl-3,4,5-trimethylaniline (ODBA) are mixed together until a clear solution i-1) is obtained.

Example 2

Example of preparation for component i):
38 g of deionised water, 47.5 g of hydroxyethylmethacrylate (HEMA), 9.5 g of mono-(2-methacroyloxy-ethyl)-Mg-phosphate (Mg-HEMA-phosphate) and 5 g of N,N-bis-β-hydroxyethyl-3,4,5-trimethylaniline (ODBA) are mixed together until a clear solution i-2) is obtained.

Example 3

Example of preparation for component i):
37 g of deionised water, 46.25 g of hydroxyethylmethacrylate (HEMA), 9.25 g of mono-(2-methacroyloxy-ethyl)-Mg-phosphate (Mg-HEMA-phosphate) and 7.5 g of N,N-bis-β-hydroxyethyl-3,4,5-trimethylaniline (ODBA) are mixed together until a clear solution i-3) is obtained.

Example 4

Example of preparation for component i):
36 g of deionised water, 45 g of hydroxyethylmethacrylate (HEMA), 9 g of mono-(2-methacroyloxy-ethyl)-Mg-phosphate (Mg-HEMA-phosphate) and 10 g of N,N-bis-β-hydroxyethyl-3,4,5-trimethylaniline (ODBA) are mixed together until a clear solution i-4) is obtained.

Example 5

Example of preparation for component ii):
40 g of 2,2-bis-4-(3-hydroxypropoxy-phenyl)-propane dimethacrylate, 25 g of triethylene glycol dimethacrylate (TEGDMA), 18 g of 2-(10'-methacrloxy-decyl)-malonic acid, 10 g of isopropylidene-bis-[2-hydroxy-3-(4-phenoxy)-propyl]-methacrylate and 7 g of hydroxyethyl methacrylate (HEMA) are mixed together until a homogeneous mixture is obtained.

Example 6

Preparation of a fixing cement:
63.5 g of glass powder (Schott) which was silanised beforehand according to the process described in EP-A-0 649 887, 17.2 g of quartz powder which was silanised beforehand according to the process described in EP-A-0 649 887, 3.7 g of OX50 (silica, Degussa) which was likewise silanised according to the above-mentioned process, 14.8 g of yttrium trifluoride and 0.8 g of di-p-methylbenzoyl peroxide are mixed to a homogeneous powder mixture.

29.2 g of 2,2-bis-4-(3-hydroxypropoxy-phenyl)-propane dimethacrylate, 69.2 g of bishydroxymethyl-tricyclo [$5.2.1.0^{2,6}$]-decane dimethacrylate and 0.6 g of N,N-bis-β-hydroxyethyl-3,4,5-trimethylaniline (ODBA) are stirred together until a clear solution is obtained.

Immediately before use, the powder mixture is intimately mixed with the liquid component in a ratio of 2.5:1.

Example 7

Use of components i)–iv) for fixing an inlay with a cement:
The adhesive strength of the restorative materials was determined by pull-off tests from dental surfaces which had been exposed by preparation of cattle teeth. The teeth were pretreated as follows:

In each case 5 cattle teeth, which had been deep-frozen after extraction, are defrosted, cleaned to remove residual gum, and the roots separated by sawing with a diamond saw. The pulp still remaining is removed with the aid of a pulp needle and the teeth are then rinsed with tap water. Plane enamel and dentine surfaces are obtained by labial grinding of the teeth on a water-cooled diamond grinding machine. The teeth are then embedded in silicone in such a way that the ground surface kept well moistened is facing upwards and a wax plate which has a punched hole 6 mm in diameter is bonded to each tooth.

The following procedure is used to apply the adhesive system according to the invention:

A film of Minitip® etching gel (component iv); Espe Seefeld) is applied to the tooth surfaces delimited by the wax plate in such a way that a continuous film is produced. After a contact time of 20 seconds, the acid-containing gel is rinsed off thoroughly with water.

With the aid of a small brush, component i) described in Example 1, 2, 3 or 4 and in reference example1 is applied to the tooth surface such that the entire surface delimited by the wax plate is wetted with said component, and this film is left to react with the surface for 20 seconds.

After blow-drying for a short period with oil-free compressed air, component ii) described in Example 5 is likewise applied with a brush to the tooth surface such that the entire surface delimited by the wax plate is coated with said component.

After 20 seconds' contact time of component ii), the cement from Example 6 prepared beforehand is applied as component iii) in a thin film over the film of component ii). The inlay prepared beforehand is simulated in this test by a screw which is pressed with its head onto the cement. After 3 minutes, curing is complete and the teeth are stored for 24 hours under moist conditions at 36° C. until the determination of the pull-off force. In order to determine the pull-off force, the screws fixed adhesively to the tooth surfaces are screwed into a holder and this in turn is clamped in a Zwick test machine of the Zwick 1435 type and the force measurement is carried out.

Example 8

Use of components i)–iv) for fixing a composite filling composition:

The preparation of the teeth including the use of component iv), and the application of components i) and ii) are carried out as described in Example 7. The composite filling material Sono-Cem® (Espe, Seefeld) prepared beforehand is applied thereto as component iii) and pressed firmly onto the tooth surface with a spherical stopper. After about 3.5 minutes, the composite and the adhesive system is cured. The filled teeth are stored under moist conditions for at least 24 hours at 36° C. until the adhesion measurement. The adhesion value determined was 2.2±0.9 MPa.

Reference Example 2

Fixing a composite filling composition with a light-curing adhesive system:

The tooth surfaces are pretreated according to the manufacturer's instructions with EBS® (Espe, Seefeld). After light-curing, the composite filling composition Pertac®-Hybrid (Espe, Seefeld) is applied to the adhesive and light-cured according to the manufacturer's instructions. The filled teeth are stored under moist conditions for at least 24 hours at 36° C. until the adhesion measurement. The adhesion value measured is 6.2±2.3 MPa.

TABLE 1

Composition and adhesion value as a function of component i)

| | Primer | | | | |
|---|---|---|---|---|---|
| Component | i-0) | i-1) | i-2) | i-3) | i-4) |
| 2-hydroxy-ethyl methacrylate [wt. %] | 50 | 48.75 | 47.5 | 46.25 | 45 |
| $H_2O$ [wt. %] | 40 | 39 | 38 | 37 | 36 |
| Mg HEMA phosphate [wt. %] | 10 | 9.75 | 9.5 | 9.25 | 9 |
| ODBA [wt. %] | 0 | 2.5 | 5 | 7.5 | 10 |
| Adhesion value to dentine (MPa) | 0.8 ± 1.0 | 4.4 ± 1.5 | 5.0 ± 1.3 | 5.8 ± 2.9 | 6.3 ± 1.8 |

Each of the references cited above is hereby incorporated in its entirety by reference.

The invention being thus described, it is clear that these methods can be modified in various ways. Said modifications are not to be considered as divergences from the spirit and purposes of the invention, and any modification which would be apparent to an expert in the field comes within the scope of the following claims.

I claim:

1. A method for fixing dental restorative materials to hard dental substance, which comprises:

a) applying onto a hard dental substance a first component which contains at least one first activator which is a constituent of a chemical initiator system and is only able to start a polymerization reaction with a second activator, and contains at least one ethylenically unsaturated compound which is capable of polymerisation;

b) applying, on top of said first component, a second component which contains at least one ethylenically unsaturated compound which is capable of polymerisation, wherein said second component otherwise contains no further activator that is able to start chemical curing with said first activator; and c) applying a dental restorative material which contains at least one second activator which, together with said first activator, is able to start a polymerisation reaction, or a cement for fixing dental restorative materials that have already cured, which contains at least one second activator which, together with said first activator, is able to start radical polymerisation.

2. The method according to claim 1, wherein before applying said first component, the dental substance is pretreated with an acid component which partially etches dental enamel and dentine.

3. The method according to claim 1, wherein the dental restorative material is selected from the group consisting of composite filling materials, inlays, onlays, crowns, bridges, ceramics, veneers and Maryland bridges.

4. The method according to claim 1, wherein said first activator is a peroxy compound, and the second activator is an amine or a proton donor; or wherein said first activator is an amine or proton donor, and the second activator is a peroxy compound.

5. An adhesive system for fixing dental restoration materials to a hard dental substance comprising the following three separate components:

i) a first component applied to a surface of the hard dental substance, said first component containing at least one first activator which is a constituent of a chemical initiator system and is only able to start a polymerization reaction with a second activator, and containing at least one ethylenically unsaturated compound which is capable of polymerisation, ii) a second component applied as a layer on said first component which contains at least one ethylenically unsaturated compound which is capable of polymerisation, wherein said second component otherwise contains no further activator that is able to start chemical curing with said first activator, and iii) a dental restorative material applied as a layer on said first and second components which contains at least one second activator which, together with said first activator, is able to start a polymerisation reaction, or a cement for fixing dental restorative materials that have already cured, which contains at least one second activator which, together with said first activator, is able to start radical polymerisation.

* * * * *